United States Patent
Gutman et al.

(10) Patent No.: US 6,288,271 B1
(45) Date of Patent: Sep. 11, 2001

(54) PROCESS FOR THE PREPARATION OF (2,2,2-TRIFLUOROETHOXY)BENZOIC ACIDS

(75) Inventors: Arie L. Gutman, Haifa; Genady Nisnevich; Eleonora Shkolnik, both of Nesher; Igor Zaltzman, Haifa, all of (IL)

(73) Assignee: FineTech, LTD, Haifa (IL)

( * ) Notice: Subject to any disclaimer, the term of this patent is extended or adjusted under 35 U.S.C. 154(b) by 0 days.

(21) Appl. No.: 09/403,384

(22) PCT Filed: Apr. 20, 1998

(86) PCT No.: PCT/IL98/00187

§ 371 Date: Jan. 18, 2000

§ 102(e) Date: Jan. 18, 2000

(87) PCT Pub. No.: WO98/47853

PCT Pub. Date: Oct. 29, 1998

(30) Foreign Application Priority Data

Apr. 21, 1997 (IL) .......................................................... 120715

(51) Int. Cl.$^7$ .................................................... C07C 63/06
(52) U.S. Cl. ........................... 562/493; 562/405; 568/626
(58) Field of Search ..................... 562/405, 493; 568/626

(56) References Cited

FOREIGN PATENT DOCUMENTS

| 0455545 | 11/1991 | (EP) . |
| 2045760 | 11/1980 | (GB) . |

OTHER PUBLICATIONS

Banitt et al., "Antiarrhythmics. N–(Aminoalkylene)trifluoroethoxybenamides and N–(Aminoalkylene)trifluoroethoxynaphthamides", *Journal of Medicinal Chemistry*, vol. 18, No. 11, (1975), 1130–1134.

Banitt et al., "Antiarrhythmics. 2. Synthesis and Antiarrhythmic Activity of N–(Piperidylalkyl) trifluoroethoxybenzamides", *Journal of Medicinal Chemistry*, vol. 20, No. 6, (1977), pp. 821–826.

Wrobel et al., "Syntheses of Tolrestat Analogues Containing Additional Substituents in the Ring and Their Evaluation as Aldose Reductase Inhibitors. Indentification of Potent, Orally Active 2–Fluoro Derivatives" *J. Med. Chem.*, vol. 34, pp. 2504–2520, (1991).

Merck Index, 12$^{th}$ Ed. Entry 4136, "Flecainide" 1996, p. 694.

Derwent Abstract of JP 053924 (Japanese Patent Application published Feb. 19, 1993), Abstract AN–096747[12].

Hawley s Condensed Chemical Dictionary, 13$^{th}$ Ed., pp. 118, 123–124, 126, & 862, Van Nostrand Reinhold, New York, 1997.

Lindley,J., "Copper Assisted Nucleophillic Substitiion of Aryl Halogen," Tetrahedron, vol. 40, pp. 1433–1456, 1984.

March, J., "Advanced Organic Chemistry, Fourth Ed.", pp. 563–565, 648–665, Wiley Interscience, New York 1992.

*Primary Examiner*—D. Margaret Seaman
(74) *Attorney, Agent, or Firm*—Needle & Rosenberg P.C.

(57) ABSTRACT

A process for producing trifluoroethoxybenzoic acids or salts thereof by reaction of halobenzoic acids or salts thereof with 2,2,2-trifluoroethanol in the presence of a strong base and copper containing materials. The compounds obtained by the process of the present invention may be used as synthetic intermediates in the pharmaceutical industry.

10 Claims, No Drawings

PROCESS FOR THE PREPARATION OF (2,2,2-TRIFLUOROETHOXY)BENZOIC ACIDS

FIELD OF THE INVENTION

The present invention relates to a process for the preparation of (2,2,2-trifluoroethoxy)benzoic acids of the general formula [I] or salts thereof

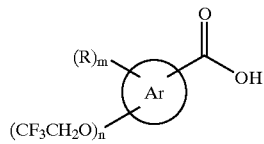

[I]

wherein

Ar represents a benzene ring,

R is hydrogen or a substituent selected from alkyl, alkoxy, alkylthio, halogen, haloalkyl, haloalkoxy, haloalkylthio, phenyl, phenoxy, benzyloxy N-substituted or N,N-disubstituted amino groups, nitro, alkoxycarbonyl, cyano, carboxyl and when m>1 the R substituents may be the same or different;

n is 1,2 or 3; and m is 0, 1, 2, 3 or 4, where n+m$\leq$5.

BACKGROUND OF THE INVENTION

Trifluoroethoxybenzoic acids of the formula [I] above are useful as intermediates in the pharmaceutical industry. For example, 2,5-bis(2,2,2-trifluoroethoxy)benzoic acid [III] is the key intermediate for the synthesis of the antiarrhythmic drug Flecainide [IV] and pharmaceutically acceptable salts thereof

[III]

[IV]

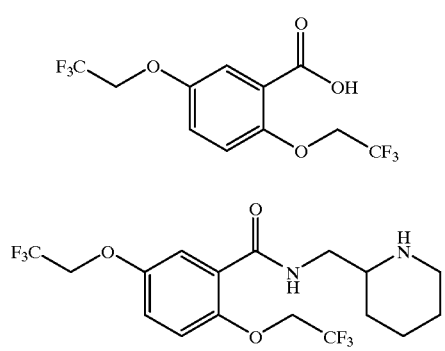

(Banitt, E. H. et al., *J. Med. Chem.* 18:1130 (1975) and 20:821 (1977); Leir, C. M. GB 2 045 760A, (1980) and The Merck Index, 12$^{th}$ Edition, 4136).

It is known that (2,2,2-trifluoroethoxy)benzoic acids [VII] can be obtained by the reaction of hydroxybenzoic acids of the general formula [V] with 2,2,2-trifluoroethyl triflate [VI] according to Scheme 1 (Banitt, E. H. et al., *J. Med. Chem.* 18:1130 (1975)).

Scheme 1

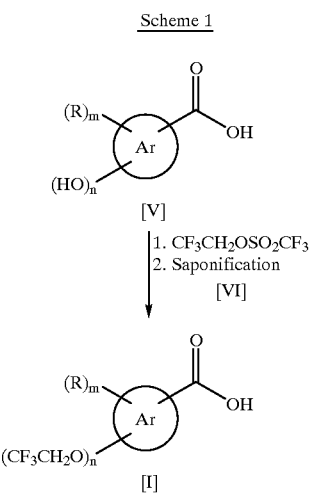

n is 1, 2 or 3

This method requires the use of trifluoroethyl triflate [VI] which is costly and not easily available commercially.

Another method involves the oxidation of the acetyl group of trifluoroethoxyacetophenones with hypochlorite as shown in Scheme 2 (Lair, C. M., GB 2045 760A). However, partial halogenation of the benzene ring may occur in this process, thus making it difficult for production of the (2,2,2-trifluoroethoxy)benzoic acids [I] as pharmaceutical precursors.

Scheme 2

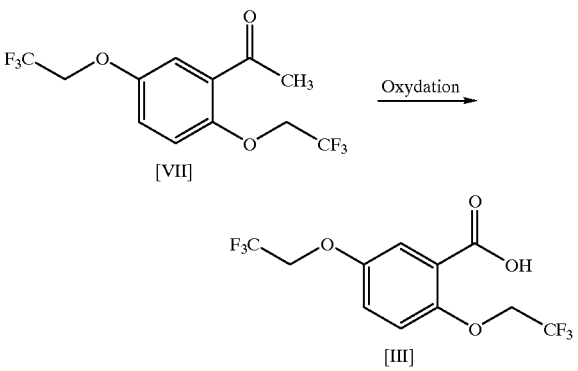

There is only one reported example of copper assisted fluoroalkoxy-de-halogenation of a 2-bromo-1-naphthalenecarboxylic acid derivative (Wrobel J. et al., *J. Med. Chem.* 34, 2504 (1991)). This example is very specific since it describes the de-halogenation of an active halogen, i.e. bromine, which is also located in a highly activated ortho position to a carboxylic group.

THE OBJECT OF THE INVENTION

It is the object of the present invention to overcome the above disadvantages of the known processes and to provide a comparatively simple, one-step process for preparing (2,2,2-trifluoroethoxy)benzoic acids [I] in good yields, employing commercially available and relatively inexpensive compounds.

DETAILED DESCRIPTION OF THE INVENTION

The above object is attained by the present invention which provides a process for the preparation of (2,2,2- trifluoroethoxy)benzoic acids of the formula [I] or salts thereof

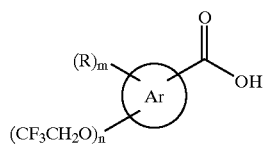

wherein
Ar represents a benzene ring;
R is hydrogen or a substituent selected from alkyl, alkoxy, alkylthio, halogen, haloalkyl, haloalkoxy, haloalkylthio, phenyl, phenoxy, benzyloxy, N-substituted or N,N-disubstituted amino groups, nitro, alkoxycarbonyl, cyano, carboxyl and when m>1 the R substituents may be the same or different;
n is 1, 2, or 3; and
m is 0, 1, 2, 3 or 4, where n+m≦5,
which process comprises reacting a halobenzoic acid or a salt thereof of the formula [II]

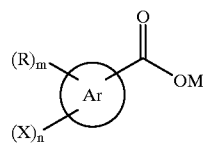

wherein
R, m and n are as defined above, and
M is hydrogen or a metal, ammonium or phosphonium cation; and
X is Cl, Br or I, and when n>1 the X substituents may be the same or different;
with 2,2,2-trifluoroethanol in the presence of a strong base and a copper containing material; if desired, followed by acidification.

(2,2,2-Trifluoroethoxy)benzoic acids [I] or salts thereof obtained in accordance with the process of the present invention may contain one or more 2,2,2-trifluoroethoxy groups. Additionally, other substituents R as defined above may be present on the aromatic ring.

As defined herein, the term "halobenzoic acid" includes benzoic acids containing one or more halogen atoms and optionally additional substituents as defined for R above.

According to a preferred embodiment of the present invention, a chloro-, bromo- or iodo-benzoic acid is reacted with a metal trifluoroethoxide in the presence of copper iodide or bromide in an aprotic solvent. Such aprotic solvent may be a dipolar aprotic solvent or an N-containing heterocycle or mixtures thereof. Examples of dipolar aprotic solvents are N,N-dimethylformamide, N-methylpyrrolidone, N,N-dimethylacetamide, DMSO and hexamethylphosphoramide. N-containing heterocyclic solvents used in the present invention are pyridine, picolines, lutidines, collidines, methylethylpyridine (MEP), other substituted pyridines, quinoline and substituted quinolines.

The reaction is preferable carried out at a temperature in the range of from ambient temperature to 170° C.

In the process of the invention, preferably at least one mole of 2,2,2-trifluoroethanol is used per each halogen atom of the halobenzoic acid [II] which is desired to be replaced by a trifluoroethoxy group. However, a large molar excess of 2,2,2-trifluoroethanol can be used in which cases this reactant may also serve as a solvent. At least one mole of 2,2,2-trifluoroethanol per mole of the strong base should be used and the mole ratio of the copper containing compound to the halobenzoic acid [II] can be in the range of 0.01 to 2.1.

Suitable copper containing materials are for example: copper salts, copper oxides, metallic copper, copper alloys, etc.

The present invention will be described in more detail with the aid of the following examples, which are merely representative and should not serve to limit the scope of the invention.

EXAMPLE 1

Synthesis of 2,5-bis(2,2,2-trifluoroethoxy)benzoic acid [III] from 5-bromo-2-chlorobenzoic acid [VIII] and 2,2,2-trifluoroethanol Scheme 3

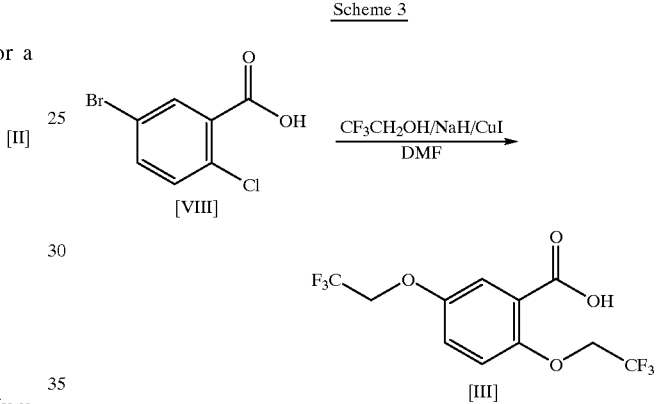

A 1 L round-bottomed flask equipped with a magnetic stirrer, a thermometer pocket, dropping funnel and a reflux condenser, was charged with 51.0 g of a 60% strength suspension of sodium hydride in mineral oil (equivalent to a total of 30.6 g (1.28 mole) of pure NaH) and 570 mL of anhydrous N,N-dimethylformamide. The mixture was cooled to room temperature in an ice-water bath and 189.5 g (1.90 mole) of anhydrous 2,2,2-trifluoroethanol were added dropwise during 40 minutes.

The mixture was cooled to room temperature and 24.8 g (0.13 mole) of anhydrous copper iodide and 59.5 g (0.25 mole) of 5-bromo-2-chlorobenzoic acid were added. The black reaction mixture was heated to about 110–115° C. and kept at this temperature for 2 hours.

The reaction mixture was cooled to room temperature and poured into a mixture of crushed ice (3 kg) and conc. hydrochloric acid (0.78 L). The mixture was vigorously stirred for 1 hour, the black precipitate was filtered off and washed at once with 200 mL of water. The obtained solid was suspended at room temperature in 1 L of 5% aqueous KOH under vigorous stirring for 15 min, followed by filtration through a Celite modified filter and washing with 100 mL of 5% aqueous KOH.

The transparent clear alkaline solution was thrice extracted with 150 mL of dichloromethane. The alkaline solution was added dropwise under vigorous stirring to mixture of 0.6 kg of ice and 0.2 L of conc. hydrochloric acid, at a temperature not higher than 0° C. and a pH 1. The mixture was stirred for 0.5 hours at these conditions. The obtained precipitate was filtered off, washed with water, collected and dried under vacuum to a constant weight. Yield: 64.7 g (81.4%) of crude 2,5-bis(2,2,2-trifluoroethoxy) benzoic acid, m.p. 116–118° C. After recrystallisation from an ethanol/water system, a product with m.p. 120–121° C. was obtained.

EXAMPLES 2 to 6

Syntheses of (2,2,2-trifluoroethoxy)benzoic acids of the general formula [X] by reacting sodium 2,2,2,-trifluoroethoxide with corresponding halobenzoic acids [IX] identified in Table 1

The procedures set forth in Example 1 were followed with the exceptions apparent from Table 1. Sodium 2,2,2-trifluoroethoxide was prepared in situ by the action of sodium hydride on 2,2,2-trifluoroethanol.

In the following examples N,N-dimethylformamide, N,N-dimethylacetamide or N-methylpyrrolidone were used as solvents. In example 5, the solvent was 2,4,6-collidine. CuX was selected from copper iodide or copper bromide. The synthesis is described in Scheme 4.

Phisico-chemical parameters of 2,2,2-trifluoroethyl esters obtained by esterification of the products of experiments 2,3,4 and 1 (see below) are identical to corresponding 2,2,2-trifluoroethyl-2,5-bis (2,2,2-trifluoroethoxy)benzoates known in the art.

Scheme 4

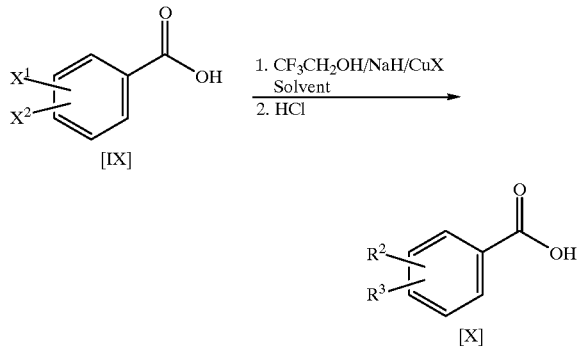

The results and the conditions are summarized in Table 1.

TABLE 1

| EXAMPLE NO. | $X^1$ | $X^2$ | $R^2$ | $R^3$ |
|---|---|---|---|---|
| 2 | 5-Br | 2-Br | 5-$CF_3CH_2O$ | 2-$CF_3CH_2O$ |
| 3 | 5-Br | 2-$CF_3CH_2O$ | 5-$CF_3CH_2O$ | 2-$CF_3CH_2O$ |
| 4 | 5-I | 2-Cl | 5-$CF_3CH_2O$ | 2-$CF_3CH_2O$ |
| 5 | 5-Cl | 2-Cl | 5-Cl | 2-$CF_3CH_2O$ |
| 6 | 5-$NO_2$ | 2-Cl | 5-$NO_2$ | 2-$CF_3CH_2O$ |

What is claimed is:

1. A process for the preparation of (2,2,2-trifluoroethoxy) benzoic acids of the formula (I) or salts thereof

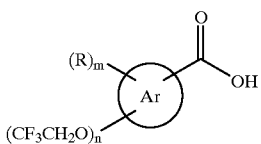

wherein

Ar represents a benzene ring,

R is hydrogen or a substituent selected from alkyl, alkoxy, alkylthio, halogen, haloalkyl, haloalkoxy, haloalkylthio, phenyl, phenoxy, benzyloxy, N-substituted or N,N-disubstituted amino groups, nitro, alkoxycarbonyl, cyano, carboxyl, and when m>1 the R substitutents may be the same or different;

n is 1, 2, 3: and m is 0,1,2,3, or 4, where m+n≦5, which process comprises reacting a halobenzoic acid or a salt thereof of the formula [II]

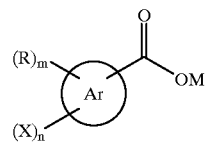

wherein

R, m and n are as defined above;

M is hydrogen or a metal, ammonium or phosphonium cation; and

X is Cl, Br, or I, and when n>1 the X substitutents may be the same or different;

with 2,2,2-trifluoroethanol in the presence of a strong base and a copper containing material; if desired, followed by acidification.

2. The process of claim 1, wherein the reaction is carried out in the presence of copper iodide and/or copper bromide.

3. The process of claim 1 wherein the 2,2,2-trifluoroethanol is reacted in a first step with a strong base to form a 2,2,2-trifluoroethoxide and, which is reacted in a second step with a halobenzoic acid or salt thereof of formula [II] in the presence of copper containing material.

4. The process of claim 1 wherein the reaction is conducted in an aprotic solvent.

5. The process of claim 4 wherein said aprotic solvent is a dipolar aprotic solvent or an N-containing heterocycle or mixtures thereof.

6. The process of claim 5 wherein the dipolar aprotic solvent is selected from the group consisting of N,N-dimethylformamide, N-methylpyrrolidone, N,N-dimethylacetamide, DMSO, hexamethylphosphoramide and mixtures thereof.

7. The process of claim 5, wherein the N-containing heterocycle is selected from the group consisting of pyridine, lutidine, collidine, and quinoline, and wherein the pyridine and quinoline are each optionally substituted.

8. The process of claim 1 wherein the strong base is selected from the group consisting of Na, NaH, $NaNH_2$, a Na and/or K alkoxide, NaOH, KOH, a fully N-substituted amidine, a guanidine, and a tetraalkylammonium hydroxide and/or alkoxide.

9. The process of claim 1 wherein said halobenzoic acid is a compound of formula [XVII] or a salt thereof and said (2,2,2-trifluoroethoxy)benzoic acid is a compound of formula [III] or a salt thereof

[XVII]

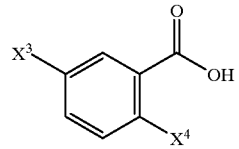

[III]

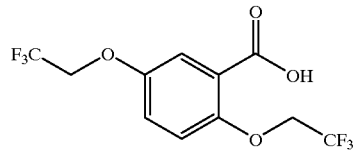

wherein:
$X^3$ Br or I, $X^4$ is Cl, Br or I, or one of $X^3$ and $X^4$ may also be $CF_3CH_2O$—; if desired, followed by acidification.

10. The process of claim 7, wherein the N-containing heterocycle is methylethylpyridine or picoline.

* * * * *

UNITED STATES PATENT AND TRADEMARK OFFICE
CERTIFICATE OF CORRECTION

PATENT NO.     : 6,288,271 B1
DATED          : September 11, 2001
INVENTOR(S)    : Gutman et al.

It is certified that error appears in the above-identified patent and that said Letters Patent is hereby corrected as shown below:

<u>Title page,</u>
Please add to the list of inventors, after "Igor Zaltman, Haifa,"
-- "Boris Tishin, Haifa," --.

Signed and Sealed this

Fourteenth Day of May, 2002

*Attest:*

JAMES E. ROGAN
*Attesting Officer*     *Director of the United States Patent and Trademark Office*